United States Patent
Wilhelm et al.

(10) Patent No.: US 6,906,032 B1
(45) Date of Patent: Jun. 14, 2005

(54) CYCLIC PEPTIDOMIMETIC UROKINASE RECEPTOR ANTAGONISTS

(75) Inventors: Olaf Wilhelm, München (DE); Horst Kessler, Garching (DE); Markus Bürgle, München (DE); Nils Potthoff, Dachau (DE); Niko Schmiedeberg, München (DE)

(73) Assignee: Wilex AG, Munich (DE)

( * ) Notice: Subject to any disclaimer, the term of this patent is extended or adjusted under 35 U.S.C. 154(b) by 562 days.

(21) Appl. No.: 10/031,401
(22) PCT Filed: Jul. 19, 2000
(86) PCT No.: PCT/EP00/06905
§ 371 (c)(1), (2), (4) Date: Jan. 18, 2002
(87) PCT Pub. No.: WO01/05811
PCT Pub. Date: Jan. 25, 2001

(30) Foreign Application Priority Data

Jul. 19, 1999 (DE) .......................................... 199 33 701

(51) Int. Cl.[7] .................................................. A61K 38/00
(52) U.S. Cl. ............................................ 514/9; 514/11
(58) Field of Search ........................................ 514/9, 11

(56) References Cited

FOREIGN PATENT DOCUMENTS

| WO | WO 97 12905 A | 4/1997 |
| WO | WO 98 21230 A | 5/1998 |
| WO | WO 98 46632 A | 10/1998 |

Primary Examiner—Christopher Tate
Assistant Examiner—Jennifer Ione Harle
(74) Attorney, Agent, or Firm—Rothwell, Figg, Ernst & Manbeck, P.C.

(57) ABSTRACT

The present invention relates to cyclic peptides as inhibitors of urokinase binding to the urokinase receptor. Said cyclic peptides are suitable as pharmaceutical active substances for disorders mediated by urokinase and its receptor.

4 Claims, 12 Drawing Sheets

Fig. 1a

Comparison of [21,29][Cys$^{21,29}$]-uPA$_{21-30}$ with $^{cyclo}$[21,29][D-Cys$^{21}$Cys$^{29}$]-uPA$_{21-30}$

Fig. 1b cyclo[21,29][D-Cys$^{21}$Cys$^{29}$]-uPA$_{21-30}$ and the corresponding peptide amide

CYCLIC PEPTIDOMIMETIC UROKINASE RECEPTOR ANTAGONISTS

The present invention relates to cyclic peptides as inhibitors of urokinase binding to the urokinase receptor, which are suitable as pharmaceutical active substances for disorders mediated by urokinase and its receptor. The substances of the invention are peptides derived from the uPA sequence and display, as ligands of the urokinase receptor (uPAR), an antagonistic action and are denoted uPAR antagonists hereinbelow.

The serine protease uPA (urokinase-type plasminogen activator) is responsible for various physiological and pathological processes, such as, for example, proteolytic degradation of extracellular matrix material which is required for the invasiveness and migration of the cells and also for tissue remodeling. uPA binds with high affinity ($K_D=10^{-10}$–$10^{-9}$M) to the membrane-bound uPA receptor (UPAR) on the cell surface.

The binding of uPA to its receptor is involved in many invasive biological processes such as, for example, metastasis of malignant tumors, implantation of trophoblasts, inflammations and angiogenesis. Therefore, uPAR antagonists are capable of inhibiting the invasiveness, metastasis and angiogenesis of tumors. uPAR antagonists may be employed as agents for the therapy of invasive and metastasizing cancers in which uPA and uPAR appear at the invasive foci of tumors (Dano et al.: The receptor for urokinase plasminogen activator: Stromal cell involvement in extracellular proteolysis during cancer invasion, in: Proteolysis and Protein Turnover, Barrett, A. J. and Bond, J., HRSG, Portland Press, London, 1994, 239), for example in cancers of the breast, lung, intestine and ovaries. Moreover, UPAR antagonists may also be employed for other purposes in which inhibition of the proteolytic activation of plasminogen is required, for example for controlling disorders such as arthritis, inflammations, osteoporosis, retinopathies and for contraception.

The uPA receptor is described in WO 90/12091 and also in the publications Ploug et al., J. Biol. Chem. 268 (1993), 17539 and Ronne et al., J. Immunol. Methods 167 (1994), 91.

uPA is synthesized as single-chain molecule (pro-uPA) and converted enzymically into an active two-chain uPA. The uPA molecule consists of three structurally independent domains, the N-terminally located growth factor-like domain (GFD, uPA 1–46), a ring structural domain (uPA 45–135) and the serine protease domain (uPA 159–141). GFD and the ring domain together form the "amino-terminal" fragment of uPA (ATF, uPA 1–135) which is generated by further proteolytic cleavage of two-chain uPA. ATF binds to the uPA receptor with a similar affinity as uPA.

The receptor-binding region of uPA extends across the region of amino acids 12 to 32, since a peptide containing the uPA amino acid residues 12 to 32 (with cysteine at position 19 being replaced by alanine) competes with ATF for binding to the uPA receptor (Appella et al., J. Biol. Chem. 161 (1987), 4437–4440). This study furthermore showed that said peptide, even after cyclization due to bridging of the two cysteine residues at positions 12 and 32, displayed an affinity for the uPA receptor. In an alternative approach, Goodson et al., (Proc. Natl. Acad. USA 91 (1994), 7129–7133) identified antagonistic uPA peptides for the uPAR by means of screening a bacteriophage peptide library. These peptides showed no obvious sequence homology to the natural uPAR-binding uPA sequence. More recent publications (Rettenberger et al., Biol. Chem. Hoppe-Seyler 376 (1995), 587–594); Magdolen et al., Eur. J. Biochem. 237 (1996), 743–751; Goretzki et al;, Fibrinolysis and Proteolysis 11 (1997), 11–19) describe further studies on the UPAR binding region of uPA. In this connection, the residues Cys19, Lys23, Tyr24, Phe25, Ile28, Trp30 and Cys31 were identified as important determinants for uPA/uPAR interaction. Said studies identified a uPA peptide with the uPA amino acids 16 to 32 as the most active inhibitor.

Magdolen et al. (1996) supra analyze the uPAR binding region of the uPA molecule by using a peptide with the uPA amino acids 14 to 32 and peptides derived therefrom. However, these peptides and also peptides used by other groups (cf. e.g. Appella et al. (1987) supra) have a relatively low affinity for UPAR.

Wo-A-94/22646 discloses linear peptides having a length of 6 to 18 amino acids which come from the region of the uPA amino acids 14 to 33. This study describes short peptides derived from uPA (uPA 21–29 and uPA 21–26) being capable of influencing the growth of keratinocytes. Although WO-A-94/22646 indicates a possible use of the claimed peptides for blocking uPA/uPAR interaction, no data or indications of such binding studies whatsoever are shown. Moreover, the linear peptides uPA 21–29 and uPA 21–26, denoted "preferred", do not contain the minimal uPAR binding region of linear uPA peptides, which includes the sequence region of amino acids 19 to 31. Thus, the influence of said short peptides on keratinocyte growth is most probably not based on a uPA/uPAR interaction.

WO 98/46632 discloses uPAR peptide inhibitors which are derived from the linear peptide uPA (19–31) and cyclic derivatives thereof and which carry D-amino acid residues in selected positions.

An example of a peptide inhibitor of this kind is the peptide cyclo[21,29][D-Cys$^{21}$,Cys$^{29}$]uPA$_{21-30}$. This peptide already has quite high affinity for uPAR (IC$_{50}$=78 nM) which is only 4 times lower than the affinity of the amino-terminal fragment of uPA (ATF=amino acids 1–135 of urokinase) which has an IC$_{50}$ of 21 nM. The corresponding peptide composed exclusively of L-amino acids, cyclo[21,29]-[Cys$^{21}$,Cys$^{29}$]-uPA$_{21-30}$, has a hundred-fold lower activity compared with ATF.

It was the object of the present invention to modify the structure of the uPAR peptide inhibitor by incorporating isostructural or/and isofunctional natural and non-natural amino acids and thus to achieve further improvement regarding the affinity for uPAR, serum stability or/and therapeutic action.

The present invention thus relates to compounds of the general structural formula (I):

wherein
X$^{21}$–X$^{30}$ are monomeric building blocks, preferably aminocarboxylic acid residues and are derived from a structure in which X$^{21}$=D-Cys, X$^{22}$=Asn, X$^{23}$=Lys, X$^{24}$=Tyr, X$^{25}$=Phe, X$^{26}$=Ser, X$^{27}$=Asn, X$^{28}$=Ile, X$^{29}$=Cys and X$^{30}$=Trp,
Y is a spacer and m is 0 or 1, and the monomeric building blocks are linked via —CONR$^1$ or —NR$^1$CO bonds, in which R$^1$ in each case independently is hydrogen, methyl or ethyl, and to pharmaceutically acceptable salts and derivatives thereof.
with the proviso that at least one of the amino acid residues X$^{21}$–X$^{30}$ of the lead structure is replaced by one of the amino acid residues listed below:

$X^{21}$: Asp, Glu, 2, 3-diaminopropionic acid (Dap), 2, 4-diaminobutyric acid (Dab), penicillamine (Pen), D-Pen, allylglycine (Alg), ornithine (Orn), Lys;

$x^{22}$. Gln, Asp, Glu;

$X^{23}$: Orn, Dap, Arg, His, citrulline (Cit), homocitrulline (Hci), norleucine (Nle);

$X^{24}$: Phe, homophenylalanine (Hph), 1,2,3,4-tetrahydroisoquinoline-3-carboxylic acid (Tic), thienylalanine (Thi), Trp, phenylglycin (Phg), 1-naphthylalanine (1-Nal), 2-naphthylalanine (2-Nal), Cha (cyclohexylalanine);

$X^{25}$: Tyr, Trp, Tic, Thi, Hph, Phg;

$X^{26}$: Thr, Val, homoserine (Hse);

$X^{27}$: Gln, Asp, Glu;

$X^{28}$: Val, Leu, 2-aminobutyric acid (Abu), tert-leucine (Tle), norvaline (Nva), Nle, α-aminoisobutyric acid (Aib), Cha;

$X^{29}$: Asp, Glu, Dap, Dab, Alg, Pen, D-Pen, Orn, Lys;

$X^{30}$: Thi, Phe, Tyr, 2-Nal, 1-Nal, octahydroindolyl-2-carboxylic acid (Oic), His, thiazolylalanine (Thia), Phg, tryptamine, tryptophanamide (Trp-NH$_2$).

Preference is given to peptides in which at least one of the amino acid residues $X^{21}$–$X^{30}$ of the lead structure has one of the meanings listed below:

$X^{21}$: D-Pen;

$X^{22}$: Gln;

$X^{23}$: Orn, Dap, Dab, Arg, Cit, Hci, Nle, His;

$X^{24}$: Phe, Thi, Hph, Phg, 1-Nal, 2-Nal, Cha;

$X^{25}$: Thi;

$X^{27}$: Asp;

$X^{28}$: Nle, Val, Cha;

$X^{29}$: Pen;

$X^{30}$: Phe, Thi, Tyr, Oic, 1-Nal, Hph, Thia, Trp-NH$_2$.

Particular preference is given to peptides in which at least one of the amino acid residues $X^{21}$–$X^{30}$ of the lead structure has one of the meanings listed below:

$X^{21}$: D-Pen;

$X^{23}$: Arg, Nle, Cit, Hci;

$X^{24}$: Phe, 1-Nal, 2-Nal, Cha,;

$X^{25}$: Thi;

$X^{28}$: Nle, Cha;

$X^{29}$: Pen;

$X^{30}$: Trp-NH$_2$.

Y is a peptidic spacer group, for example a peptidic spacer group composed of one or more amino acids, for example poly-Lys, or another spacer group, for example a polyethylene glycol group. The peptide may be coupled to support substances via the group Y.

The peptides of the invention are cyclic peptides having a nine-membered ring, where at least 2, preferably at least 3 and particularly preferably at least 4, of the amino acid residues forming the ring have a sequence from the uPA region 22 to 28.

The present invention further relates to compounds of the general structural formula (I):

wherein $X^{21}$–$X^{30}$ are monomeric building blocks, preferably aminocarboxylic acid residues and are derived from a structure in which $X^{21}$=D-Cys, $X^{22}$=Asn, $X^{23}$=Lys, $X^{24}$=Tyr, $X^{25}$=Phe, $X^{26}$=Ser, $X^{27}$=Asn, $X^{28}$=Ile, $X^{29}$=Cys and $X^{30}$=Trp, Y is a spacer and m is 0 or 1, and the monomeric building blocks are linked via —CONR$^1$ or —NR$^1$CO bonds, in which R$^1$ in each case independently is hydrogen, methyl or ethyl, and to pharmaceutically acceptable salts and derivatives thereof, with the proviso that at least one of the amino acid residues $X^{21}$–$X^{30}$ of the lead structure is replaced by a non-proteinogenic amino acid residue, with the resulting compounds preferably having increased protease stability, in particular increased stability against physiological proteases, for example proteases present in blood or tissue, such as, for example, plasmin, or/and proteases present in the digestive tract such as, for example, pepsin, trypsin or chymotrypsin, compared with the lead structure. Preferably, at least the amino acid residue Lys$^{23}$ is replaced by a non-proteinogenic amino acid, i.e. by a non-genetically encoded amino acid such as, for example, Orn, Dap, Dab, Cit, Hci or Nle.

Suitable UPAR antagonists are, apart from peptides of the structural formula (I), also pharmaceutically acceptable salts and derivatives thereof. Suitable derivatives are in particular those compounds which have modified reactive side chain groups or/and modified N- or C-terminal groups, for example amino or carboxyl groups. Examples of such modifications are acylation, for example acetylation of amino groups, or/and amidation or esterification of carboxyl groups, for example amidation of the C-terminal amino acid. The monomeric building blocks are linked via NR$^1$CO or CONR$^1$ carboxamide bonds, i.e. the direction of the peptide sequence can be reversed (retropeptides). R$^1$ may be hydrogen, as in native polypeptides. On the other hand, however, R$^1$ may also be an alkyl radical, for example methyl or ethyl, and in particular methyl, since N-alkylation of the amide bond can often have a strong effect on the activity (cf. e.g. Levian-Teitelbaum et al., Biopolymers 28 (1989), 51–64). Unless stated otherwise, the α-aminocarboxylic acids are employed as monomeric building blocks in the form of L-enantiomers.

The peptides of the invention are cyclic compounds, with the monomeric building blocks $X^{21}$ and $X^{29}$ being bridged with one another. Said bridging may take place, for example, via the side chains of the particular α-aminocarboxylic acid residues and bridging via disulfide bonds, for example between two cysteine residues, is particularly preferred. However, other types of cyclization between amino acid side chains are also possible, for example amide bonds between an amino acid with an amino side group, for example ornithine or Lys, and an amino acid with a carboxyl side chain such as, for example, Asp or Glu. Furthermore, the disulfide bridge may also be replaced by an alkylene bridge, in order to increase chemical stability. Moreover, linkages of an amino acid side chain to the peptide backbone, for example linkage of an amino side group, for example an (ω-amino side chain, to the C-terminal end, and linkage of a carboxyl side group to the N-terminal end are also possible. A linkage of N- and C-terminus is also possible. The peptides of the invention are obtainable by chemical synthesis, as illustrated in the examples.

Furthermore, the present invention relates to a pharmaceutical composition which contains as active substance at least one peptide or polypeptide as defined above, where appropriate together with pharmaceutically common carriers, excipients or diluents. The peptides or polypeptides of the invention are in particular used for preparing uPAR antagonists which are also suitable for controlling of disorders associated with uPAR expression, in particular for controlling tumors. Furthermore, the peptides of the invention, as well as the lead structure cyclo[21,29][D-Cys$^{21}$,Cys$^{29}$]-uPA$_{21-30}$, can be employed as inhibitors of angiogenesis.

The present invention further relates to the use of the uPAR peptide antagonists of the invention for preparing targeting vehicles, for example liposomes, viral vectors, etc., for cells expressing UPAR. Targeting may be carried out for diagnostic applications for controlled transport of labeling groups, for example radioactive or nonradioactive labeling groups.

On the other hand, targeting may be carried out for therapeutic applications, for example for transporting pharmaceutical active substances, for example also for transporting nucleic acids for gene therapy.

The pharmaceutical compositions of the invention may be present in any form, for example as tablets, as coated tablets or in the form of solutions or suspensions in aqueous or nonaqueous solvents. The peptides are administered preferably orally or parenterally in liquid or solid form. The preferred carrier medium used for administration in liquid form is water which, where appropriate, contains stabilizers, solubilizers or/and buffers commonly used for injection solutions. Such additives are, for example, tartrate or borate buffer, ethanol, dimethyl sulfoxide, complexers such as, for example, EDTA, polymers such as, for example, liquid polyethylene oxide, etc.

Examples of solid carrier substances which may be employed for administration in solid form are starch, lactose, mannitol, methylcellulose, talc, highly dispersed silicon oxide, high molecular weight fatty acids such as, for example, stearic acid, gelatin, agar, calcium phosphate, magnesium stearate, animal and plant fats or solid, high molecular weight polymers such as, for example, polyethylene glycols. Furthermore, the formulations for oral application may also contain flavorings and sweeteners, if desired.

The therapeutic compositions of the invention may also be present in the form of complexes, for example with cyclodextrins such as, for example, γ-cyclodextrin. The dose administered depends on the age, state of health and weight of the patient, on the type and seriousness of the disease, on the type of treatment, on the frequency of administration and the type of desired action. The daily dose of the active compound is usually 0.1 to 50 mg/kilogram of body weight.

Typically, 0.5 to 40 and preferably 1.0 to 20 mg/kg/day in one or more doses are sufficient in order to achieve the desired effects.

The examples and figures described below are intended to further illustrate the invention.

In this connection,

FIG. 1 shows the comparison of the affinities of peptides cyclo[21,29][Cys$^{21,29}$]-uPA$_{21-30}$ and cyclo[21–29][D-Cys$^{21}$,Cys$^{29}$]-uPa$_{21-30}$ (a) and cyclo[21,29][Cys$^{21,29}$] uPa$_{21-30}$ and the corresponding peptide amide (b), respectively;

FIG. 4 shows the stability of the peptides cyclo[19,31]-uPA$_{16-32}$, cyclo[21,29][D-Cys$^{21}$, Tic$^{25}$,Cys$^{29}$]-uPA$_{21-30}$ and cyclo[21,29]-[D-Cys$^{21}$, Cys$^{29}$]uPA$_{21-30}$ in human serum (a) and heparinized human blood (b);

EXAMPLES

1. Methods 1.1 Solid Phase Peptide Synthesis Linear peptides were synthesized on a 2-chlorotrityl resin (Barlos et al., Int. J. Pept. Protein Res. 37 (1991), 513 to 520) or a trityl chloride polystyrene resin using an Applied Biosystems Model 431 A peptide synthesizer or a multiple peptide synthesizer Model Syro II (MultiSynTech). Applying the orthogonal Fmoc strategy (Carpino and Han, J. Org. Chem. 37 (1972), 3404–3409; Fields and Noble, Int. J. Peptide Protein Res. 35 (1990), 161–214), the amino acid side chains were blocked with the protective groups trityl (Asn, Cys, Gln and His), tert-butyloxycarbonyl (Lys and Trp), tert-butyl (Asp, Glu, Ser, Thr and Tyr), acetamidomethyl (Cys) and 2,2,5,7,8-pentamethylchroman-6-sulfonyl or 2,2,4,6,7-pentamethyldihydrobenzofuran-5-sulfonyl (Arg). Coupling was carried out in dimethylformamide at room temperature using a three-fold excess of 2-(1H-benzotriazol-1-yl)-1,1,3,3-tetramethyluronium tetrafluoroborate/1-hydroxybenzotriazole/Fmoc amino acid with 2.5 equivalents of N-ethyldiisopropylamine in N-methylpyrrolidone. The Fmoc group was removed by sequentially treating the resins with an excess of 40% and 20%, respectively, piperidine in dimethylformamide. The peptides were cleaved off and the protective groups of the side chains were removed at the same time by treatment with 93% trifluoroacetic acid/5% triisopropylsilane/3% H$_2$O (0° C./1 h; room temperature/1 h). In the case of 2,2,5,5,7,8-pentamethylchroman-6-sulfonyl-protected Arg groups, the peptides were incubated at room temperature for an additional 12 h. The crude peptides were precipitated with diethyl ether at −30° C., dissolved in methanol, precipitated as before, dissolved in tert-butanol and lyophilized. Tryptophan-containing peptides were additionally treated with 5% acetic acid for 2 h prior to lyophilization.

The peptides were purified by HPLC using a reverse phase C-18 column (Nucleosil 1005-C18) or a YMC-Pack ODS column. The cyclization was carried out by forming a disulfide bridge. The oxidation required for this was carried out by taking up 0.1 to 0.3 mg/ml purified linear peptides in 80% water and 20% DMSO (v/v) and removing the solvent under reduced pressure after 10 h. The cyclic peptides were then again purified by HPLC as described before.

1.2 Mass Spectrometry and Amino Acid Analysis

The purified and desalted peptides were analyzed on the HPLC system 140 B (Applied Biosystems, Foster City, USA). UV absorption was measured at 206 nm using a UVIS 200 (Linear Instruments, Reno, USA) detector. The chromatography was carried out on an Aquapore 3 μ(Applied Biosystems, Foster City, USA) reverse phase column (1 mm×50 mm) with a flow rate of 20 μl/min. The solvent system was 0.1% TFA in water (A) and 0.1% TFA in acetonitrile (B). The HPLC system was coupled to an atmospheric pressure ionization source which was connected to an API III tandem quadrupole instrument (Sciex, Perkin Elmer, Thornhill, Canada).

The quadrupole m/z scale was calibrated using the ammonium adducts of polypropylene glycol. The average masses were calculated from the m/z peaks in the charge distribution profiles of the multiply charged ions (Covey et al., Rapid Commun. Mass Spectrom. 2 (1988), 249–256; Fenn et al., Science 246 (1989), 64–71).

The amino acid analysis was carried out according to the ninhydrin method using the analysis system 6300 (Beckman Instruments, Fullerton, USA), after hydrolyzing the peptides by the TFA-HCl vapor-phase method (Tsugita et al., J. Biochem. 102 (1987), 1593–1597), which allows quantitative determination of the peptide concentration.

1.3 Flow Cytometry

The capacity of the synthetic peptides for inhibiting uPA/uPAR interaction was determined using the human promyeloid cell line U937 as source for cellular native uPAR by means of flow cytometry on a FACScan flow cytometer (Becton-Dickinson, Heidelberg, Germany) (Chuchulowski et al., Fibrinolysis 6, Suppl. 4 (1992), 95–102; Magdolen et al., (1996), supra). The U937 cells were stimulated with 1 mM phorbol 12-myristate 13-acetate (PMA) for 48 h. After stimulation with PMA, the U937 cells express considerable amounts of cell surface-associated uPAR.

The stimulated cells were treated with 50 mM glycine-HCl, 0.1 NaCl, pH 3.6 at room temperature for 1 min, in order to dissociate endogenous receptor-bound uPA. Subsequently, the acidic buffer was neutralized by 0.5 M HEPES, 100 mM NaCl, pH 7.5. The cells were then immediately washed twice with PBS/0.1% bovine serum albumin (BSA) and centrifuged at 300×g at room temperature for 10 min. The cells were resuspended in PBS/0.1% BSA, adjusted to a concentration of $10^6$ cells per ml and incubated simultaneously with 16 ng of FITC-conjugated pro-uPA and different amounts of the synthetic peptides at room temperature for 45 min. Prior to analysis, propidium iodide, a fluorescent dye binding specifically double-stranded DNA, was added to each sample, in order to determine the viability of the analyzed U937 cells. Damaged, propidium iodide-labeled cells were excluded from the analysis.

1.4 Solid Phase uPAR/uPA Binding Test

In addition to the analyses by flow cytometry, a solid phase ATF ligand binding test was carried out to determine the interactions of synthetic peptides with uPAR. For this, microtiter plates were coated with recombinant human uPAR from CHO cells (Wilhelm et al., FEBS Lett. 337 (1994), 131–134; Magdolen et al., Elektrophoresis 16 (1995), 813–816) and the remaining protein-binding sites were saturated with 2% BSA (w/v). After incubation with the samples (0.6 ng of ATF together with 15 µg of synthetic peptide per ml) and two or more washing steps, the amount of ATF which had bound to uPAR immobilized on the microtiter plate was determined using a biotinylated monoclonal mouse antibody against the ATF ring domain (No. 377, American Diagnostica, Greenwich, Conn., USA) and subsequently adding avidine-peroxidase conjugate and 3,3',5,5'-tetramethylbenzidine/$H_2O_2$ as peroxidase substrate. The presence of synthetic peptides competing with ATF binding to UPAR reduces conversion of the chromogenic substrate.

1.5 Determination of Peptide Stability in Body Fluids

The stability of uPA-derived peptides in human serum or complete blood was assayed in vitro.

Human sera were prepared by allowing venous blood to coagulate without anti-coagulant in polypropylene tubes at 37° C. for 45 min. The clots adhering to the vessel wall were removed using a plastic stick and removed by centrifugation at 1200×g at room temperature for 12 min. The serum in the supernatant was removed and either used freshly for stability studies or frozen in aliquots at −20° C. for further use.

For stability studies in human complete blood, coagulation of venous blood was inhibited by heparin sodium (1 000 IU per 10 ml of complete blood), and the blood was used freshly. The peptides to be tested were added to the body fluids in the form of peptide-mixture stock solutions ($\geq$1 µg per peptide in $H_2O$) at a concentration of 5 µg/100 µl of serum or 200 µl of complete blood (per peptide) and incubated at 37° C. for various times. Prior to HPLC analysis, complete blood incubations were centrifuged at 16 000×g at room temperature for 5 min and the plasma in the supernatant was removed.

Sera and plasmas were prepurified via HLB precolumns (Waters GmbH, Oasis HLB extraction cartridge 1 $cm^3$/30 mg) prior to HPLC analysis. For this purpose, 100 µl of liquid were diluted with PBS to 1 ml and applied to said HLB precolumns equilibrated with 1 ml of 100% methanol and 1 ml of $H_2O$. The columns were washed with 1 ml of 5% methanol in $H_2O$ and eluted with 1 ml of 100% methanol. The first 200 µl (4 drops) of the eluate were discarded as void volume. The next 500 µl of eluate were diluted with 500 µl of PBS and analyzed by HPLC. The remaining 300 µl of the eluate were discarded. HPLC analysis was carried out using a YMC-5 $C_{18}$ analytical column and a 20–60% gradient of $H_2O$, 0.1% trifluoroacetic acid and acetonitrile, 0.1% trifluoroacetic acid over 30 min and detecting the analytes at 220 nm.

1.6 Determination of Protease Resistance

The sensitivity of peptides against the attack of various proteases of the digestive tract was determined in vitro using purified enzymes under suitable buffer conditions. In general, 10 µg of peptide were incubated in a 100 µl volume with 2 µg of protease at 37° C. for 30 min under the buffer conditions for the activity controls as stated by the manufacturer. After incubation and dilution with 300 µl of $H_2O$ the mixtures were analyzed directly, without prepurification via a precolumn, by HPLC using a 20–60% gradient of $H_2O$, 0.1% trifluoroacetic acid and acetonitrile, 0.1% trifluoroacetic acid.

Pepsin (Sigma, Deisenhofen, Germany) was incubated with peptides in 52 mM HCl. Incubations with trypsin (Sigma) were carried out in 63 mM sodium phosphate pH 7.6. Chymotrypsins α, β, γ, δ (ICN) were incubated in 50 mM $CaCl_2$ and 40 mM Tris/HCl pH 7.8. This was followed by incubating with bacteriae proteinase K in unbuffered water. The positive control used was the peptide cyclo[19, 31]-uPA$_{16-32}$ which corresponds to the original sequence of the uPA omega loop except for the cysteine bridge. The peptide sensitivity against the tissue protease plasmin (Sigma) was assayed in mixtures with 10 or 5 µg of peptides and 0.05 U of plasmin in 100 µl of 200 mM sodium phosphate pH 7.5 at 37° C. and a 30 min incubation period.

2. Results

Figure 1A:
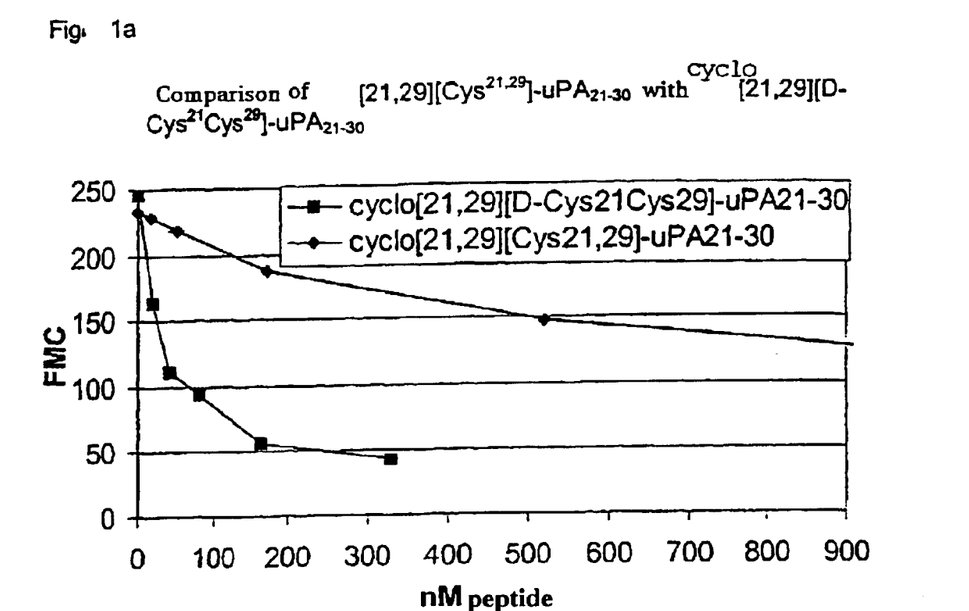

2.1 Inhibitory Action of the Peptide Cyclo[21,29][D-Cys$^{21}$, Cys$^{29}$]uPA$_{21-30}$ FIG. 1a depicts the inhibitory action of the peptide cyclo[21,29][D-Cys$^{21}$,Cys$^{29}$]uPA$_{21-30}$ compared with the cyclic peptide cyclo[21,29][Cys$^{21,29}$]-uPA$_{21-30}$ which consists exclusively of L-amino acids. The IC$_{50}$ of the cyclic peptide with D-Cys at position 21 was determined to 78 nM, while the IC$_{50}$ of the cyclic peptide composed of only L-amino acids was determined to 2 260 nM. In comparison therewith, the IC$_{50}$ of the amino-terminal fragment of uPA (uPA amino acids 1 to 135) is 21 nM.

2.2 Synthesis of Modified uPA Peptides

Figure 1B:
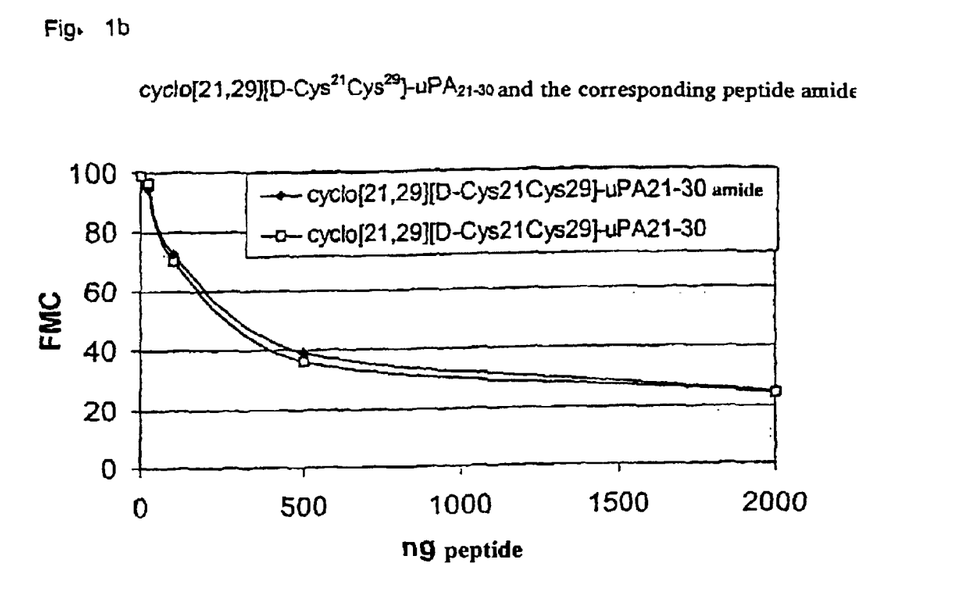
Figure 2:
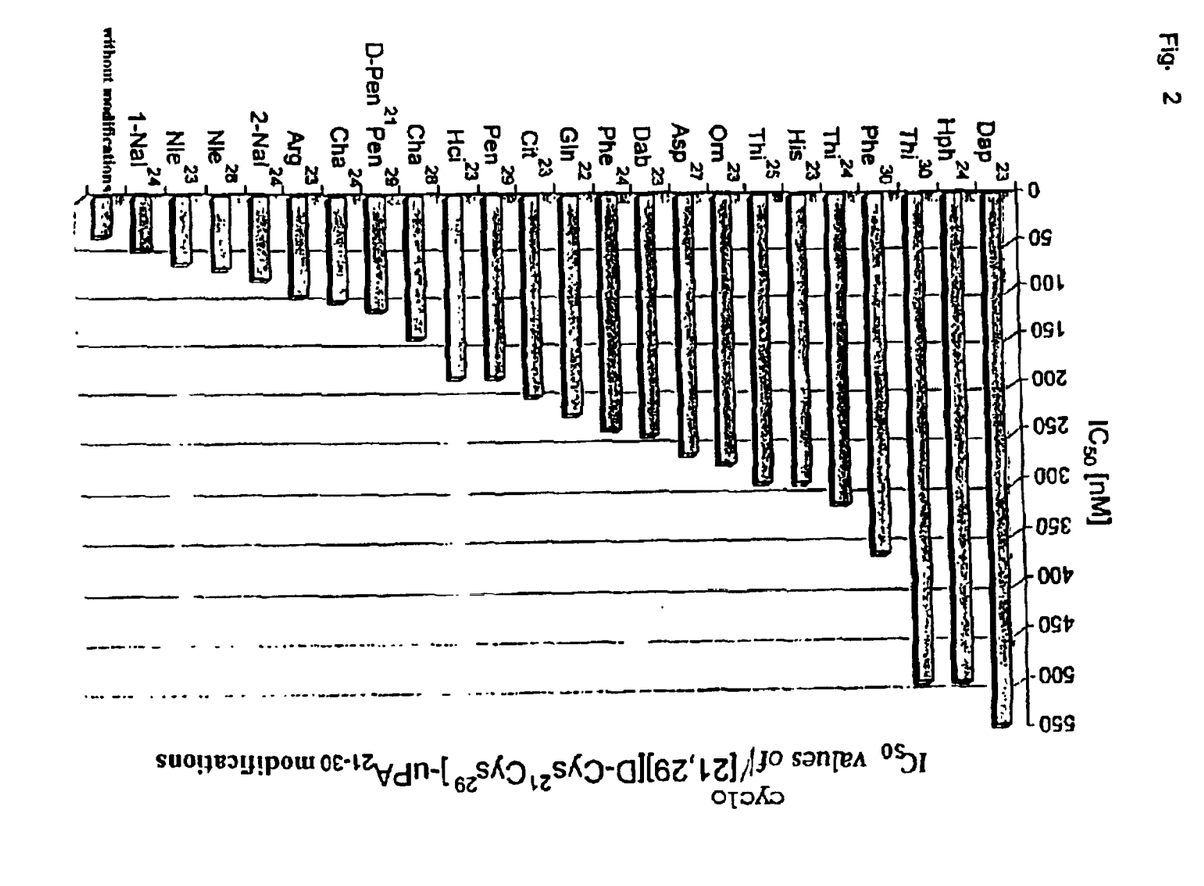
FIG. 2 shows IC$_{50}$ values of modifications of the lead structure cyclo[21,29][D-Cys$^{21}$,Cys$^{29}$]uPA$_{21-30}$.

Using cyclo[21,29][D-Cys$^{21}$,Cys$^{29}$]uPA$_{21-30}$ as lead structure, further cyclic peptides were prepared, in which particular amino acids were substituted by other, in particular non-proteinogenic amino acids. The relative activities compared with the lead structure are depicted in FIGS. 1b and 2.

Figure 3:
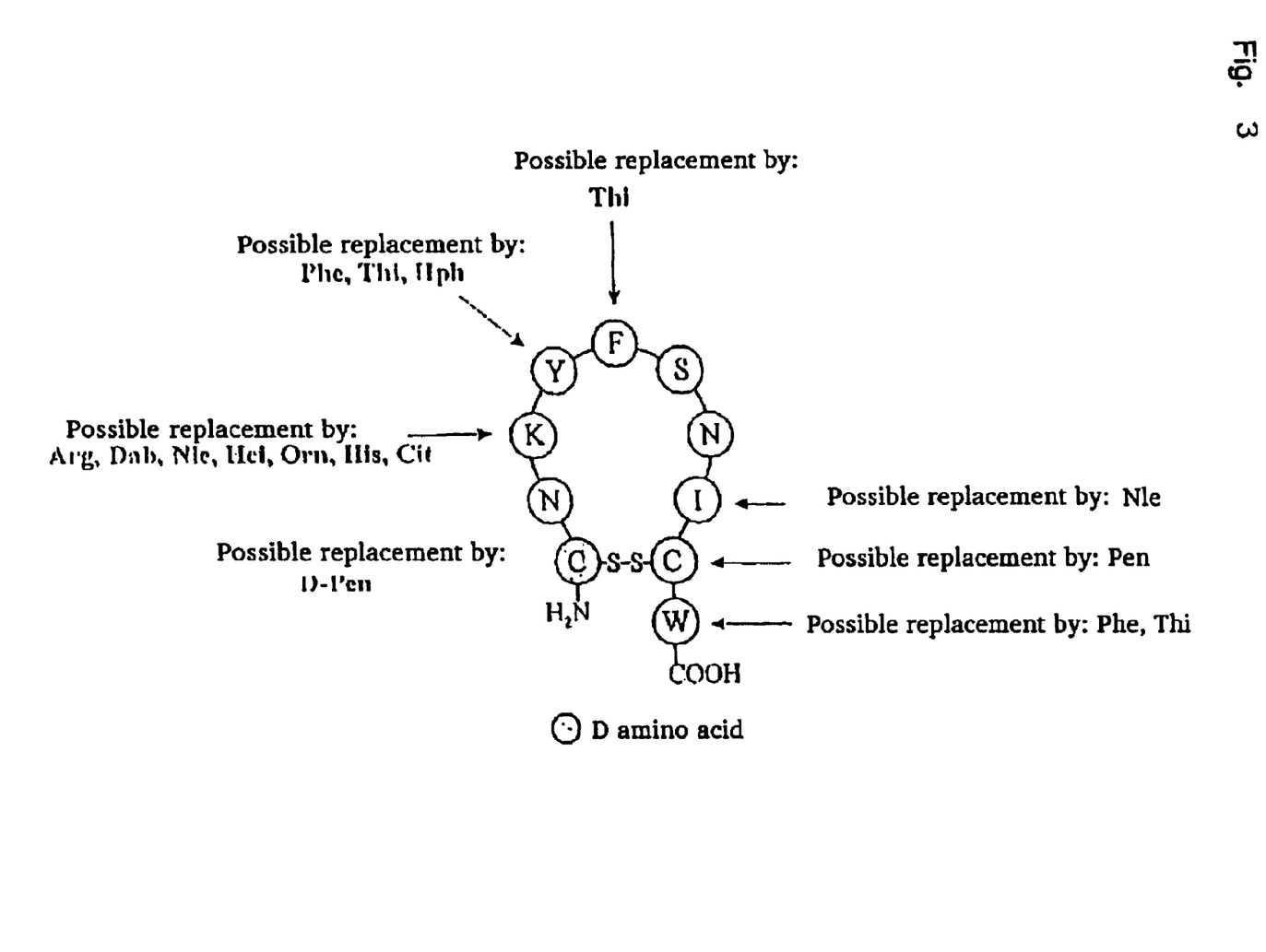
FIG. 3 shows a diagrammatic representation of preferred lead structure modifications.

FIG. 3 depicts examples of particularly preferred modifications of the lead structure.

Figure 4A:
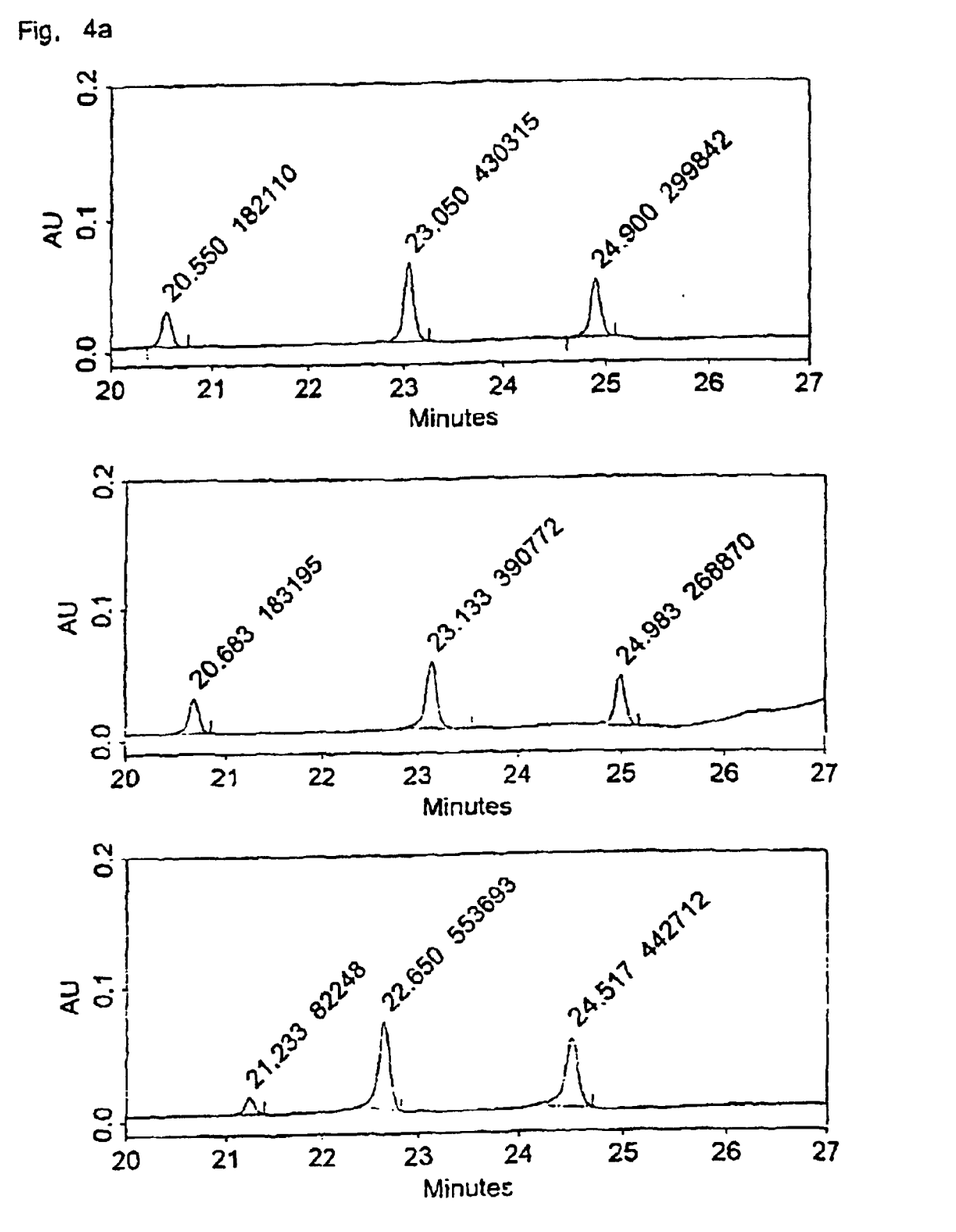
Figure 4B:
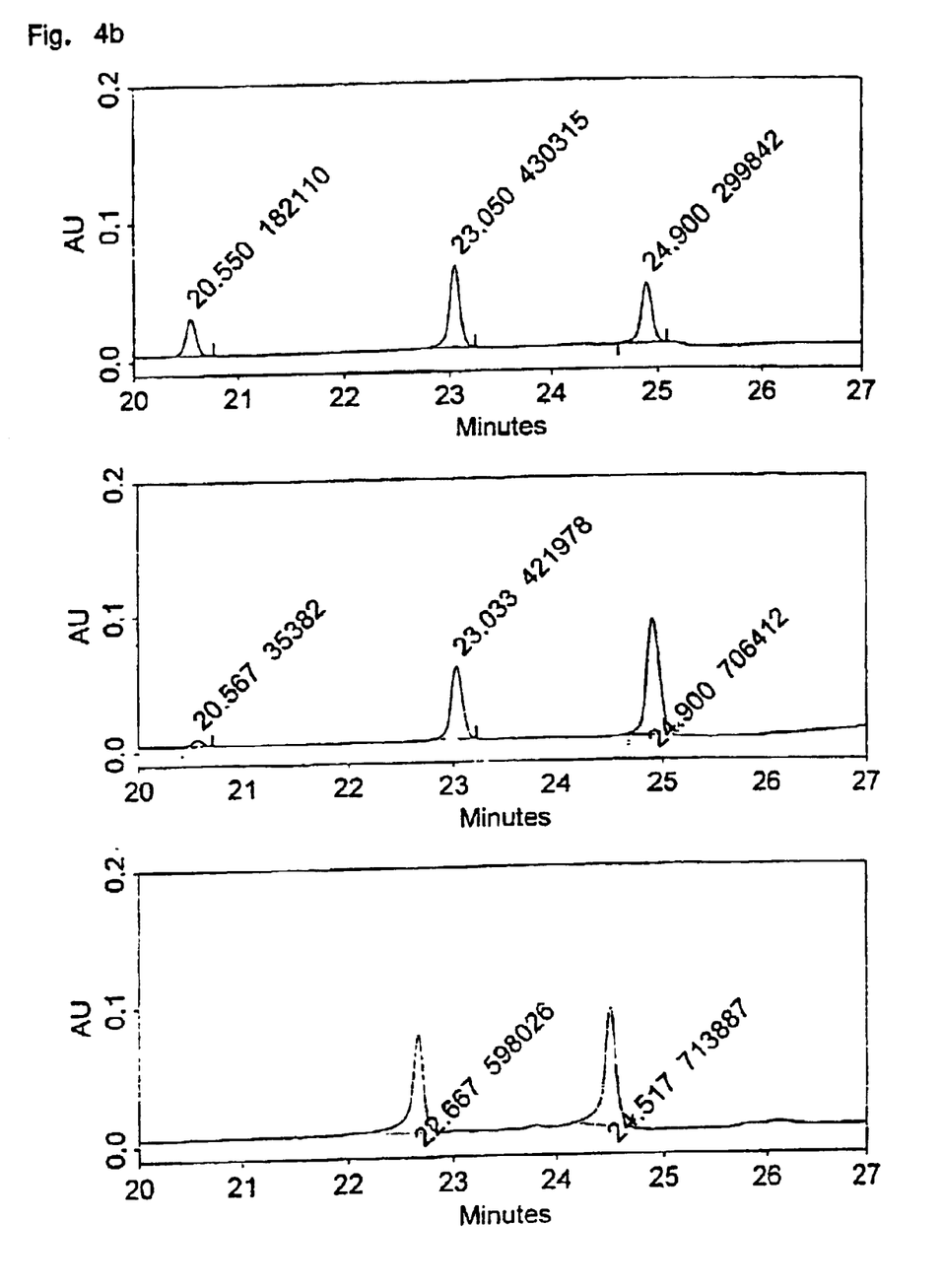

2.3 Results of the Studies on Peptide Stability in Human Serum and Complete Blood The stability of peptides cyclo[19,31]-uPA$_{16-32}$ (A), cyclo [21,29][D-Cys$^{21}$,Tic$^{25}$,Cys$^{29}$]-uPA$_{21-30}$ (B) and cyclo[21, 29][D-Cys$^{21}$,Cys$^{29}$]-uPA$_{21-30}$ (C) in human serum and heparinized human blood was assayed. FIGS. 4a and 4b depict the results of these experiments. The peaks at 20.5 min correspond to peptide A, the peaks at 23.0 min correspond to peptide B and the peaks at 24.9 min correspond to peptide C.

The stability of the peptides in human serum (FIG. 4a) was studied by adding a mixture of in each case 12.5 µg of the peptides to about 250 µl of serum. 100 µl thereof were diluted with PBS to 1 ml, prepurified on an HLB precolumn and analyzed immediately by HPLC (middle profile). A further 100 µl were analyzed after 20.5 h of incubation at 37° C. (bottom profile). As a control, in each case 5 µg of the peptides were admixed with 1 ml of PBS and analyzed (top profile). The peak at 21.2 min corresponds to a nonidentified metabolite.

The stability in heparinized human blood (FIG. 4b) was studied by adding 750 µl of freshly prepared heparinized human blood to 37.5 µg of the peptides. Immediately thereafter, 375 µl were removed by centrifugation. 100 µl of the plasma supernatant were analyzed (middle profile). The remaining 375 µl were incubated with gentle agitation at 37° C. for 20.5 h and then analyzed (bottom profile). As a control, 5 µg of the peptides had already been admixed with 1 ml of PBS and analyzed (top profile).

After incubation in human serum at 37° C. for 20.5 h peptide A (cyclo[19,31]-uPA$_{16-32}$) could no longer be detected. Instead a new peak with relatively longer retention time (FIG. 4a, bottom HPLC profile, RT 21.233 min) appeared, which corresponds presumably to a metabolite of A. In contrast, the relative retention times and peak integrals of peptides B (cyclo[21,29][D-Cys$^{21}$Tic$^{45}$Cys$^{29}$]-uPA$_{21-30}$) and C (cyclo[21,29][D-Cys$^{21}$Cys$^{29}$]-uPA$_{21-30}$) remained nearly the same, after exposure to human serum. This allows the conclusion to be reached that the chemical identity and concentration of the two peptides are unaltered after a 20.5-hour exposure to human serum.

Exposing the peptides to freshly isolated heparinized complete blood over 20.5 h, too, showed the instability of A. In this case, it was not possible to detect either the unaltered substance or a suspected metabolite. In contrast, the peaks of peptides B and C appeared stable in human blood. Compared with the PBS control, the A peak appears already substantially reduced in the sample worked up and analyzed immediately after addition to complete blood. Apparently, the short period between addition of the peptides and prepurification on precolumns (10–15 min) was sufficient to degrade a substantial part of the amount of peptide added (>80%).

The peak integrals of the two D-Cys derivatives B and C from plasma are distinctly larger than in the PBS control, although they were used at the same concentration, based on total volumes of PBS and complete blood. After incubation, however, the peptides were analyzed only in the plasma after removing the blood cells. This may be regarded as an indication that the D-Cys derivatives are distributed mainly in the plasma but are unable to penetrate or bind blood cells in a significant manner.

2.4 Stability of uPA Peptides Against Plasmin

The peptide lead structure cyclo[21,29][D-Cys$^{21}$Cys$^{29}$]-uPA$_{21-30}$ and modifications thereof at position 23, cyclo[21,29][D-Cys$^{21}$Orn$^{23}$Cys$^{29}$]-uPA$_{21-30}$ (ornithine), cyclo[21,29][D-Cys$^{21}$Dab$^{23}$Cys$^{29}$]-uPA$_{21-30}$(2,4-diaminobutyric acid), cyclo[21,29][D-Cys$^{21}$Dap$^{23}$Cys$^{29}$]-uPA$_{21-30}$(2,3-diaminopropionic acid), cyclo[21,29][D-Cys$^{21}$Nle$^{23}$Cys$^{29}$]-uPA$_{21-30}$ (norleucine) and cyclo[21,29][D-Cys$^{21}$Arg$^{23}$Cys$^{29}$]-uPA$_{21-30}$ (arginine) were tested for the sensitivity to attack by the tissue protease plasmin. The lead structure cyclo[21,29][D-Cys$^{21}$Cys$^{29}$]-uPA$_{21-30}$ contains plasmin cleavage site known from urokinase, i.e. the peptide bond between Lys$^{23}$ and Tyr$^{24}$.

Figure 5:
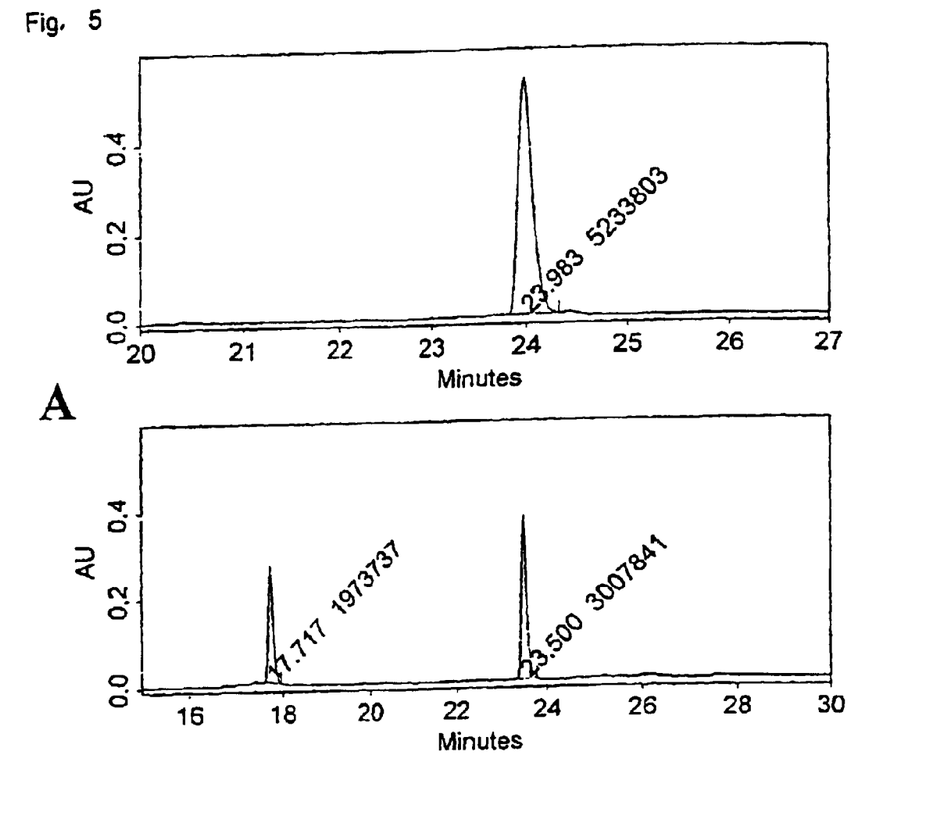
FIG. 5 shows the plasmin resistance of uPA peptides after substitution of Lys$^{23}$ by non-proteinogenic amino acids.

FIG. 5 depicts HPLC profiles of peptide variants prior to (top profiles) and after (bottom profiles) incubation with plasmin. Part (A) of the figure depicts the unaltered lead structure cyclo[21,29][D-Cys$^{21}$Cys$^{29}$]-uPA$_{21-30}$ with lysine at position 23, (B) the ornithine-substituted variant cyclo[21,29][D-Cys$^{21}$Orn$^{23}$Cys$^{29}$]-uPA$_{21-30}$, (C) the diaminobutyric acid-substituted variant cyclo[21,29][D-Cys$^{21}$Dab$^{23}$Cys$^{29}$]-uPA$_{21-30}$, (D) the diaminopropionic acid-substituted variant cyclo[21,29][D-Cys$^{21}$Dap$^{23}$Cys$^{29}$]-uPA$_{21-30}$, (E) the norleucine-substituted variant cyclo[21,29][D-Cys$^{21}$Nle$^{23}$Cys$^{29}$]-uPA$_{21-30}$ and (F) the arginine-substituted variant cyclo[21,29][D-Cys$^{21}$Arg$^{23}$Cys$^{29}$]-uPA$_{21-30}$. The protease plasmin appears in the bottom profiles in each case at approx. 17.5 min.

After the incubation of cyclo[21,29][D-Cys$^{21}$Cys$^{29}$]-uPA$_{21-30}$ with plasmin and HPLC analysis of the products, a new unknown peak appeared in addition to the peak of the unaltered lead structure. The sum of both peak integrals corresponded to 93.5% of the peak integral of the unaltered lead structure. Accordingly, the new peak was very likely the plasmin cleavage product of cyclo[21,29][D-Cys$^{21}$Cys$^{29}$]-uPA$_{21-30}$. Of all the peptides which were modified at position 23 and were active with respect to competing with uPA for binding to uPAR, the diaminobutyric acid-, ornithine- and norleucine-substituted peptides proved stable against plasmin (FIG. 5). In the case of the Arg$^{23}$-substituted variant a new peak appeared after incubation with plasmin, whose retention time was nearly identical to that of the plasmin metabolite of the unaltered lead structure, i.e. the Arg$^{23}$-substituted variant is plasmin-sensitive. When exposing the diaminopropionic acid-substituted variant to plasmin, two small unidentified peaks appeared at approx. 21 min, whose retention time differs greatly from the retention times of the plasmin metabolites of the lead structure and those of the Arg$^{23}$ variant. Correspondingly, it is questionable whether the small 21 min peaks indeed represent specific plasmin cleavage products of the Dap$^{23}$ variant.

Substitution of lysine at position 23 of the cyclo[21,29][D-Cys$^{21}$Cys$^{29}$]-uPA$_{21-30}$ lead structure by non-proteinogenic amino acids may generate stability against the tissue protease plasmin, without substantially altering the biological activity.

2.5 Anti-Angiogentic Effectiveness

Thorax aortae were obtained from 1-to 2-month-old Wistar rats and immediately transferred into a culture dish containing. serum-free medium (RPMI). The tissue surrounding the aorta was carefully removed. Aorta rings of 1 mm in length were prepared and thoroughly washed with serum-free medium. Before embedding the aorta rings in Matrigel, the bottom of each well was coated with 80 µl of gel solution. After gel formation, the aorta rings were transferred into the well, positioned and fixed by overlaying with 70 µl of gel solution. After gel formation, various amounts of the particular test peptide were introduced into the wells. Controls studied were medium alone, medium with growth supplements and medium with growth supplements and control peptide. The cultures were kept at 35° C. for 5 days and then studied.

The test peptides were cyclo[21,29][D-Cys$^{21}$,Cys$^{29}$]-uPA$_{21-30}$ and cyclo [21,29][D-Cys$^{21}$,Nle$^{23}$Cys29]uPA$_{21-30}$ in dosages of 0.001, 0.1, 1, 10, 25 and 50 µg/ml. The test peptides displayed distinct anti-angiogenetic actions in the in-vitro tissue culture assay. Capillary formation was found to be inhibited in the concentration range of about 1 µg/ml and higher. Capillary budding, i.e. the number and length of newly formed capillaries, could be reduced at a peptide concentration of 30 µg/ml by a factor of about 3 to 4, compared with inactive control peptides.

What is claimed is:

1. A compound of the general structural formula (I):

wherein $X^{21}$–$X^{30}$ are monomeric building blocks, preferably aminocarboxylic acid residues and are derived from a structure in which $X^{21}$=D-Cys, $X^{22}$=Asn, $X^{23}$= Dap, Dab, or Nle, $X^{24}$=Tyr, $X^{25}$=Phe, $X^{26}$=Ser, $X^{27}$= Asn, $X^{28}$=Ile, $X^{29}$=Cys and $X^{30}$=Trp, Y is a spacer and m is 0 or 1, and the monomeric building blocks are linked via —CONR$^1$ or —NR$^1$CO bonds, in which R$^1$ in each case independently is hydrogen, methyl or ethyl, and pharmaceutically acceptable salts and derivatives thereof.

2. The compound as claimed in claim 1, characterized in that at least 2 of the amino acid residues $X^{22}$, $X^{24}$, $X^{25}$, $X^{26}$, $X^{27}$, $X^{28}$ and $X^{30}$ have the same side chain as an amino acid at the same position in the native UPA sequence.

3. The compound as claimed in claim 2, characterized in that at least 2 of the amino acid residues $X^{24}$, $x^{25}$, $x^{28}$ and $x^{30}$ have the same side chain as in the native UPA sequence.

4. A pharmaceutical composition, which contains as active substance at least one compound as claimed in claim 1, where appropriate together with pharmaceutically common carriers, excipients or diluents.

* * * * *

UNITED STATES PATENT AND TRADEMARK OFFICE
CERTIFICATE OF CORRECTION

PATENT NO. : 6,906,032 B1  Page 1 of 1
DATED : June 14, 2005
INVENTOR(S) : Wilhelm et al.

It is certified that error appears in the above-identified patent and that said Letters Patent is hereby corrected as shown below:

<u>Title page,</u>
Item [*] Notice, replace "562" with -- 503 --.

Signed and Sealed this

Twenty-eighth Day of March, 2006

JON W. DUDAS
*Director of the United States Patent and Trademark Office*

SEQUENCE LISTING

<160> NUMBER OF SEQ ID NOS: 1

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: uPAR peptide inhibitor

<400> SEQUENCE: 1

```
Cys Asn Lys Tyr Phe Ser Asn Ile Cys Trp
1               5                   10
```